United States Patent
Suzuki et al.

(10) Patent No.: US 9,766,174 B2
(45) Date of Patent: *Sep. 19, 2017

(54) OPTICAL MEASURING DEVICE AND OPTICAL MEASURING METHOD

(71) Applicant: Sony Corporation, Tokyo (JP)

(72) Inventors: Shunpei Suzuki, Chiba (JP); Shingo Imanishi, Kanagawa (JP); Gakuji Hashimoto, Kanagawa (JP); Suguru Dowaki, Kanagawa (JP)

(73) Assignee: Sony Corporation, Tokyo (JP)

( * ) Notice: Subject to any disclaimer, the term of this patent is extended or adjusted under 35 U.S.C. 154(b) by 147 days.

This patent is subject to a terminal disclaimer.

(21) Appl. No.: 14/301,917

(22) Filed: Jun. 11, 2014

(65) Prior Publication Data

US 2014/0293273 A1    Oct. 2, 2014

Related U.S. Application Data

(63) Continuation of application No. 13/042,930, filed on Mar. 8, 2011, now Pat. No. 8,780,338.

(30) Foreign Application Priority Data

Mar. 10, 2010  (JP) ................ 2010-053785

(51) Int. Cl.
*G01N 21/00* (2006.01)
*G01N 15/14* (2006.01)
(Continued)

(52) U.S. Cl.
CPC ..... *G01N 15/1434* (2013.01); *G01N 15/1459* (2013.01); *G01N 21/64* (2013.01);
(Continued)

(58) Field of Classification Search
CPC ........... G01N 15/1434; G01N 15/1459; G01N 2015/1493; G01N 2021/4716; G01N 21/64; G01N 21/645
See application file for complete search history.

(56) References Cited

U.S. PATENT DOCUMENTS 3,705,771 A    12/1972  Friedman et al.
3,830,569 A    8/1974   Meric
(Continued)

FOREIGN PATENT DOCUMENTS

JP    49-125097    11/1974
JP    52-029789    3/1977
(Continued)

OTHER PUBLICATIONS

Japanese Office Action issued Oct. 1, 2013 in corresponding Japanese Patent Application No. 2010-053785.
(Continued)

*Primary Examiner* — Kara E Geisel
*Assistant Examiner* — Rufus Phillips
(74) *Attorney, Agent, or Firm* — K&L Gates LLP

(57) ABSTRACT

Disclosed herein is an optical measuring device including: a light applying section configured to apply exciting light to a sample flowing in a channel; and a scattered light detecting section configured to detect scattered light generated from the sample irradiated with the exciting light on the downstream side of the sample in the traveling direction of the exciting light; the scattered light detecting section including a scattered light separating mask for separating the scattered light into a low numerical aperture component having a numerical aperture not greater than a specific value and a high numerical aperture component having a numerical aperture greater than the specific value; a first detector for detecting the low numerical aperture component; and a
(Continued)

second detector for detecting the high numerical aperture component.

14 Claims, 9 Drawing Sheets

(51) Int. Cl.
  *G01N 21/64* (2006.01)
  *G01N 21/47* (2006.01)
(52) U.S. Cl.
  CPC ... *G01N 21/645* (2013.01); *G01N 2015/1493* (2013.01); *G01N 2021/4716* (2013.01)

(56) References Cited

U.S. PATENT DOCUMENTS

| | | | |
|---|---|---|---|
| 3,850,525 | A | 11/1974 | Kaye |
| 4,273,443 | A | 6/1981 | Hogg |
| 4,341,471 | A | 7/1982 | Hogg et al. |
| 4,512,197 | A * | 4/1985 | von Gutfeld ...... G01N 29/2418 73/601 |
| 4,735,504 | A | 4/1988 | Tycko |
| 5,073,790 | A * | 12/1991 | Ogawa ................. G01D 5/2492 396/125 |
| 5,125,737 | A | 6/1992 | Rodriguez et al. |
| 6,344,298 | B1 * | 2/2002 | Starodubov .......... G02B 5/1857 250/492.1 |
| 6,850,324 | B1 | 2/2005 | De Metz |
| 7,420,669 | B2 | 9/2008 | Sopori et al. |
| 8,208,144 | B2 * | 6/2012 | Palumbo ................ G01N 21/49 250/201.2 |
| 2007/0145995 | A1 | 6/2007 | Sopori |

FOREIGN PATENT DOCUMENTS

| | | |
|---|---|---|
| JP | 55-124028 | 9/1980 |
| JP | 60-115858 | 6/1985 |
| JP | 07-192297 | 7/1995 |
| JP | 08-054388 | 2/1996 |
| JP | 11-023447 | 1/1999 |
| JP | 2003-515724 | 5/2003 |
| JP | 2006-230333 | 9/2006 |
| JP | 2007-263894 | 10/2007 |

OTHER PUBLICATIONS

H. Nakauchi, "To Use Flexibly Flow Cytometry", Shujunsha, 2nd Edition, 2006.

* cited by examiner

OPTICAL MEASURING DEVICE AND OPTICAL MEASURING METHOD

CROSS REFERENCES TO RELATED APPLICATIONS

The present application is a continuation of U.S. patent application Ser. No. 13/042,930 filed Mar. 8, 2011, which application claims priority to Japanese Priority Patent Application JP 2010-053785 filed in the Japan Patent Office on Mar. 10, 2010, the entire content of which is hereby incorporated by reference.

BACKGROUND

The present application relates to an optical measuring device and method for identifying a sample such as minute particles, and more particularly to a technique for identifying the kind etc. of the sample by detecting fluorescence and scattered light generated from the sample irradiated with light having a specific wavelength.

In the case of identifying biological minute particles such as cells, microorganisms, and liposomes, an optical measuring method using flow cytometry (flow cytometer) is generally used (see Hiromitsu Nakauchi, supervisor, "Cell Engineering Separate Volume, Experimental Protocol Series, Flow Cytometry Jiyujizai," Second Ed., Shujunsha Inc., (Aug. 31, 2006), for example). The flow cytometry is an analyzing method of individually identifying a plurality of minute particles flowing in a line in a channel by applying laser light having a specific wavelength to the minute particles and detecting fluorescence or scattered light generated from each minute particle irradiated with the laser light.

More specifically, a sample liquid containing a plurality of minute particles as an object to be measured and a sheath liquid flowing around the sample liquid form a laminar flow in a channel to line the minute particles contained in the sample liquid. In this condition, laser light is applied toward the channel, so that the minute particles are individually passed through the laser beam. At this time, each minute particle is excited by the laser light to generate fluorescence and/or scattered light, which are/is detected by using a photodetector such as a CCD (Charge Coupled Device) or a PMT (Photo-Multiplier Tube). The light detected by the photodetector is converted into an electrical signal and digitized to perform statistical analysis, thereby determining the kind, size, structure, etc. of each minute particle.

The scattered light to be measured in this flow cytometry is broadly classified into "forward scattered light" and "side scattered light." The forward scattered light is light scattering at substantially the same angle as the incident angle of the laser light, and the side scattered light is light scattering in a direction perpendicular to the traveling direction of the laser light. For example, in the case that the sample as an object to be measured is a cell, it is widely known that the forward scattered light reflects information on the size of the cell and that the side scattered light reflects information on the form and internal structure of the cell. An analyzing device using this principle has already been developed (see Japanese Patent Laid-open Nos. 2006-230333 and 2007-263894, for example).

FIG. 11 is a schematic diagram showing the configuration of an existing optical measuring device 100 having a mechanism for measuring side scattered light. In the optical measuring device 100, exciting light 111 is applied from a light source 101 toward a detection area 109 of an analytical chip 102, so that scattered light is generated from a minute particle 110 in the detection area 109. A side scattered component 112 of this scattered light is detected on the upstream side of the analytical chip 102 in the traveling direction of the exciting light 111. More specifically, the side scattered component 112 generated from the minute particle 110 is passed through a condenser lens 103 and a pinhole 104 and next detected by a scattered light detector 105 such as a PMT.

On the other hand, a forward scattered component 113 of the scattered light is detected on the downstream side of the analytical chip 102 in the traveling direction of the exciting light 111 as in the case of detection of fluorescence. More specifically, the forward scattered component 113 generated from the minute particle 110 is condensed with fluorescence and the exciting light 111 by an objective lens 106. The exciting light 111 is next removed by an exciting light shielding mask 107. The forward scattered component 113 is next separated from the fluorescence by an LPF (Long Pass Filter) 108 and next detected by a detector (not shown).

SUMMARY

However, the existing technique mentioned above has the following problem. That is, in the existing optical measuring device 100 shown in FIG. 11, it is necessary to adjust three focal points, that is, the focal point of a condenser lens for condensing the exciting light 111, the focal point of the objective lens 106 for detecting the forward scattered component 113 and the fluorescence, and the focal point of the condenser lens 103 for detecting the side scattered component 112. Accordingly, the adjustment of an optical system in the existing device is troublesome and a size reduction in the device is difficult.

It is accordingly desirable to provide an optical measuring device and method which can facilitate the adjustment of the optical system and can reduce the size of the device.

In accordance with an embodiment, there is provided an optical measuring device including a light applying section configured to apply exciting light to a sample flowing in a channel; and a scattered light detecting section configured to detect scattered light generated from the sample irradiated with the exciting light on the downstream side of the sample in the traveling direction of the exciting light; the scattered light detecting section including a scattered light separating mask for separating the scattered light into a low NA (numerical aperture) component having a numerical aperture less than or equal to a specific value and a high NA component having a numerical aperture greater than the specific value; a first detector for detecting the low NA component; and a second detector for detecting the high NA component.

As described above, the scattered light detecting section includes the scattered light separating mask for separating the incident scattered light into the low NA component and the high NA component. Accordingly, a side scattered component of the scattered light can be detected on the downstream side of the sample in the traveling direction of the exciting light. As a result, it is not necessary to provide an optical system for detecting a side scattered component on the upstream side of the sample in the traveling direction of the exciting light.

Preferably, the scattered light detecting section further includes a relay lens system for forming a conjugate plane on the scattered light separating mask.

Preferably, the numerical aperture of the low NA component is less than or equal to 0.3.

Preferably, the numerical aperture of the high NA component is greater than or equal to 0.6.

Preferably, the scattered light separating mask transmits or reflects the low NA component having a numerical aperture less than or equal to 0.3, reflects or transmits the high NA component having a numerical aperture greater than or equal to 0.6, and absorbs the other component having a numerical aperture greater than 0.3 and less than 0.6.

Preferably, the optical measuring device further includes an analytical chip having a microchannel, wherein the light applying section applies the exciting light to the sample flowing in the microchannel.

Preferably, the scattered light detecting section further includes an exciting light shielding mask for removing the exciting light.

Preferably, the optical measuring device further includes a fluorescence detecting section configured to detect fluorescence generated from the sample irradiated with the exciting light; and a filter provided between the sample and the fluorescence detecting section/the scattered light detecting section for separating the fluorescence and the scattered light from each other.

In accordance with another embodiment, there is provided an optical measuring method including the steps of applying exciting light to a sample as an object to be measured; separating scattered light generated from the sample irradiated with the exciting light into a low NA component having a numerical aperture less than or equal to a specific value and a high NA component having a numerical aperture greater than the specific value on the downstream side of the sample in the traveling direction of the exciting light; and detecting the low NA component and the high NA component separately.

According to the embodiment, of the scattered light generated from the sample irradiated with the exciting light, not only a forward scattered component, but also a side scattered component is detected on the downstream side of the sample in the traveling direction of the exciting light. Accordingly, the optical system can be easily adjusted and the optical measuring device can be reduced in size.

Additional features and advantages are described herein, and will be apparent from the following Detailed Description and the figures.

DETAILED DESCRIPTION

Embodiments of the present application will be described below in detail with reference to the drawings.

Some preferred embodiments of the present application will now be described in detail with reference to the attached drawings. It should be noted that the present application is not limited to the following preferred embodiments. The preferred embodiments will be described in the following order.

1. First Preferred Embodiment
(Optical measuring device for detecting side scattered light on the downstream side of a sample in the traveling direction of exciting light)

2. Second Preferred Embodiment
(Optical measuring device having an NA separating mask in place of a light shielding mask)

3. Third Preferred Embodiment
(Optical measuring device having an NA separating mask located at the pupil of an objective lens)

1. First Preferred Embodiment

General Configuration of the Optical Measuring Device

Figure 1:
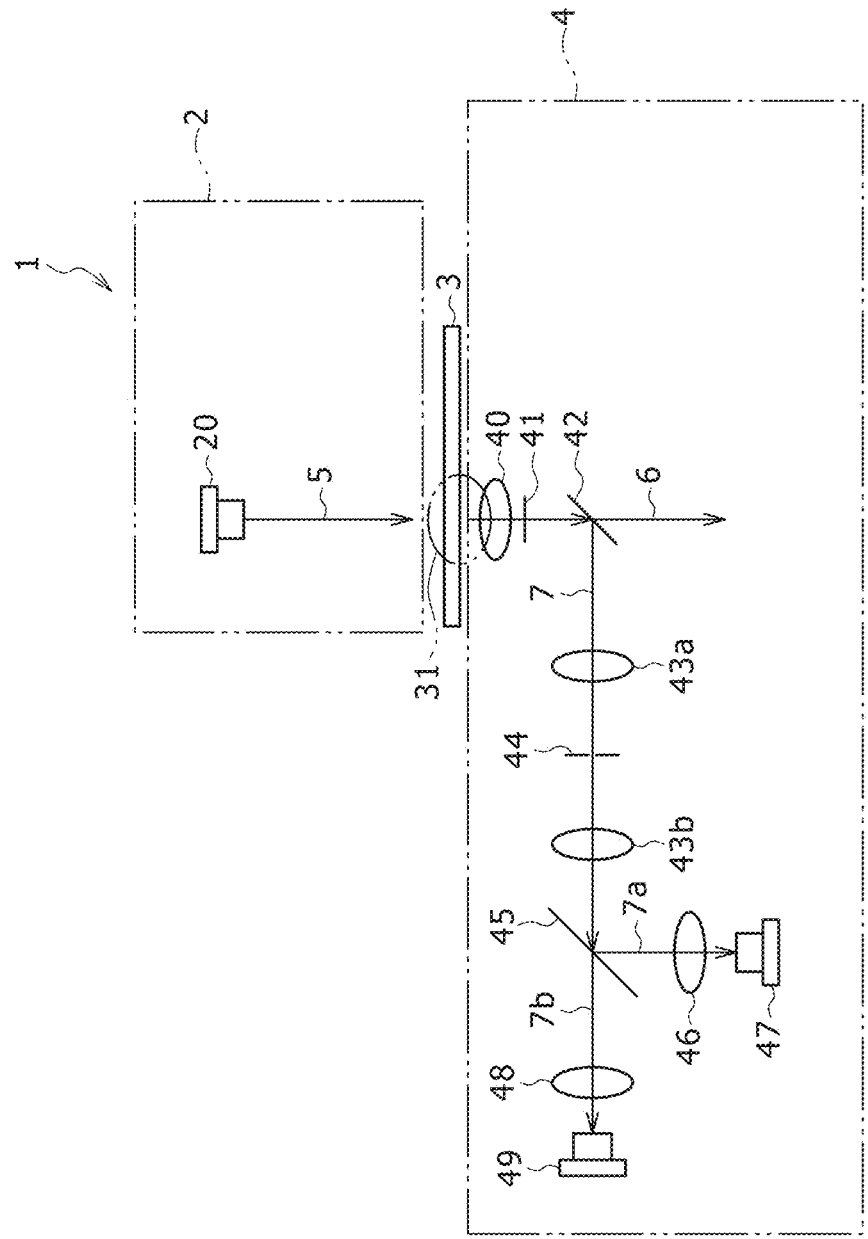
FIG. 1 is a schematic diagram showing the configuration of an optical measuring device according to a first preferred embodiment.

FIG. 1 is a schematic diagram showing the configuration of an optical measuring device 1 according to a first preferred embodiment. As shown in FIG. 1, the optical measuring device 1 is a device for measuring a sample such as minute particles by using an analytical chip 3 having a microchannel. The optical measuring device 1 includes a light applying section 2 and a detecting section 4. For example, the optical measuring device 1 is used in a microchip type FACS (Fluorescence Activated Cell Sorting) system.

[Configuration of the Light Applying Section 2]

The light applying section 2 functions to apply exciting light 5 to the sample flowing in the channel of the analytical chip 3. The light applying section 2 includes a light source 20 for generating the exciting light 5. The light source 20 may be suitably selected from any kinds of light sources according to measurement content or the like. Examples of the light source 20 may include a laser diode, SHG (Second Harmonic Generation) laser, gas laser, and high-luminance LED (Light Emitting Diode).

Also, the light applying section 2 may further include an objective lens (not shown) for condensing the exciting light 5 toward the sample and a bandpass filter having characteristics such that it transmits only light having a specific wavelength and reflects light having the other wavelengths. In the case that the bandpass filter is provided, unwanted light components can be removed. Accordingly, the bandpass filter is effective especially in the case that an LED or a white light source is used to generate the exciting light 5. The light applying section 2 has a configuration such that it can apply light having a specific wavelength (the exciting light 5) to the sample. Further, the kind and location of various optical components such as a light source, lens, and optical filter in the light applying section 2 may be suitably selected and the configuration of the light applying section 2 is not limited to the above-mentioned configuration.

Analytical Chip 3

The analytical chip 3 used in the optical measuring device 1 includes a microchannel in which the sample flows. The microchannel has a configuration such that a sample liquid containing the sample and a sheath liquid flowing around the sample liquid form a laminar flow to line the sample in a measurement area irradiated with the exciting light 5. The analytical chip 3 may further include a recovered liquid collecting portion for collecting a sample as an object to be taken and a waste liquid collecting portion for collecting any samples other than the sample as the object to be taken. In this case, a plurality of branch channels communicating with these portions are provided downstream of a detection area 31.

Configuration of the Detecting Section 4

The detecting section 4 functions to detect fluorescence 6 and scattered light 7 generated from the sample irradiated with the exciting light 5. The detecting section 4 includes a fluorescence detector (not shown) for detecting the fluorescence 6 generated from the sample and scattered light detectors 47 and 49 for detecting the scattered light 7 generated from the sample. Further, an objective lens 40, an exciting light shielding mask 41, and an LPF (Long Pass Filter) 42 are provided between the sample and the fluorescence detector so as to be arranged in this order from the sample side.

Further, a relay lens system (lenses 43*a* and 43*b*), an NA separating mask 45, and condenser lenses 46 and 48 are provided between the LPF 42 and the scattered light detectors 47 and 49 so as to be arranged in this order from the LPF 42 side. Further, as required, a pinhole 44 may be provided between the lens 43*a* and the 43*b* constituting the relay lens system.

(Objective Lens 40)

The objective lens 40 functions to condense the fluorescence 6 and the scattered light 7 generated from the sample. Preferably, the objective lens 40 has a high numerical aperture (NA), thereby allowing high-sensitivity measurement of the feeble fluorescence 6 and the feeble scattered light 7 generated from the sample as an object to be measured.

(Exciting Light Shielding Mask 41)

By applying the exciting light 5 to the sample, the scattered light 7 having the same wavelength as that of the exciting light 5 and the fluorescence 6 having a wavelength different from that of the exciting light 5 are generated from the sample. Then, the fluorescence 6 and the scattered light 7 enter the detecting section 4. Further, the exciting light 5 not applied to the sample, but passed through the analytical chip 3 also enters the detecting section 4. Since the fluorescence 6 and the scattered light 7 generated from the sample are much feebler than the exciting light 5, it is necessary to remove the exciting light 5 from the light that has entered the detecting section 4. In order to remove the exciting light 5 from the light that has entered the detecting section 4, the exciting light shielding mask 41 is provided between the objective lens 40 and the LPF 42 in the optical measuring device 1 according to the first preferred embodiment.

Figure 2:
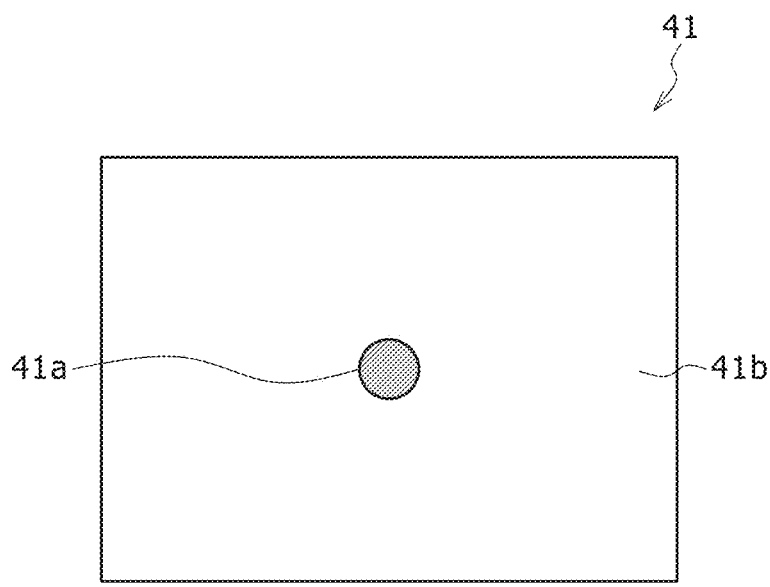
FIG. 2 is a schematic view showing the configuration of an exciting light shielding mask used in the first preferred embodiment.

FIG. 2 is a schematic view showing the configuration of the exciting light shielding mask 41. As shown in FIG. 2, the exciting light shielding mask 41 has a reflecting area 41*a* at the central portion and a transmitting area 41*b* surrounding the reflecting area 41*a*. In the exciting light shielding mask 41, the reflecting area 41*a* functions to shield the exciting light 5 having a low numerical aperture (NA) and the transmitting area 41*b* functions to transmit the fluorescence 6 and the scattered light 7 emerging from the sample at a wide angle. After passing through the transmitting area 41*b*, the fluorescence 6 and the scattered light 7 enter the fluorescence detector and the scattered light detectors 47 and 49, respectively.

The larger the reflecting area 41*a* of the exciting light shielding mask 41, the more excellent the effect of shielding the exciting light 5. However, in this case, the sensitivity to the fluorescence 6 and the scattered light 7 small in signal intensity is reduced. To detect the fluorescence 6 and the scattered light 7 with high sensitivity, the size of the reflecting area 41*a* of the exciting light shielding mask 41 is preferably set to a minimum size allowing the NA of the exciting light 5 to be blocked.

If the size of the reflecting area 41*a* is much greater than the NA of the exciting light 5, there is a possibility that the detection sensitivity to the fluorescence 6 and the scattered light 7 may be reduced. If the size of the reflecting area 41*a* is equal to or less than the NA of the exciting light 5, there is a possibility that the exciting light 5 having a high beam intensity may be mixed into the light passing through the transmitting area 41*b*, causing a trouble in measuring the fluorescence 6 and the scattered light 7. Further, the mixing of stray light (exciting light 5) due to internal reflection in the optical components may also cause a trouble in measuring the fluorescence 6 and the scattered light 7. Accordingly, it is preferable to remove the stray light and the exciting light component other than the scattered light.

(LPF 42)

The LPF 42 functions to separate the fluorescence 6 and the scattered light 7 from each other. The LPF 42 has a configuration such that it reflects only light having a specific wavelength and transmits light having the other wavelengths. More specifically, the LPF 42 reflects the scattered light 7 and transmits the fluorescence 6.

(Fluorescence Detector)

The fluorescence detector is not especially limited provided that it can detect the fluorescence 6 generated from the sample. Examples of the fluorescence detector may include a PD (Photo-Diode), CCD (Charge Coupled Device), and PMT (Photo-Multiplier Tube).

(Relay Lens System)

The relay lens system is composed of two lenses 43*a* and 43*b* disposed at a predetermined interval. The relay lens system has a magnification of 1 and forms a conjugate plane with respect to the pupil of the objective lens 40 on the NA separating mask 45. The pinhole 44 is optionally provided between the lens 43*a* and the lens 43*b*, so as to remove a disturbance component. For example, a light shielding plate may be used as the pinhole 44.

(NA Separating Mask 45)

Figure 3:
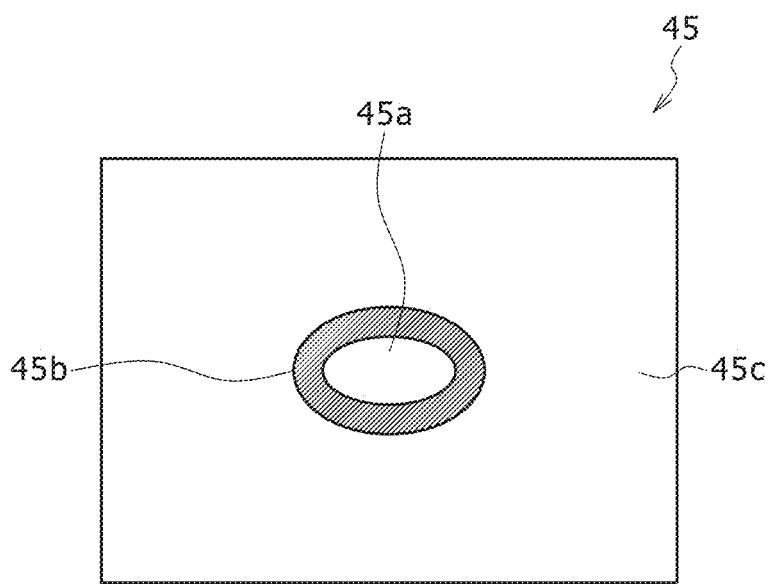
FIG. 3 is a schematic view showing the configuration of an NA separating mask used in the first preferred embodiment.

FIG. 3 is a schematic view showing the configuration of the NA separating mask 45. The NA separating mask 45 functions to separate the incident scattered light 7 into a side scattered component 7*a* and a forward scattered component 7*b*. For example, the NA separating mask 45 may be configured so as to transmit a low NA component having a numerical aperture less than or equal to a specific value and reflect a high NA component having a numerical aperture greater than the specific value. Alternatively, the NA separating mask 45 may be configured so as to reflect the low NA component and transmit the high NA component.

As a modification, the NA separating mask 45 may be configured so that the low NA component has a numerical aperture less than or equal to 0.3 and the high NA component has a numerical aperture greater than or equal to 0.6, wherein the remaining component having a numerical aperture greater than 0.3 and less than 0.6 is not detected. That is, in the range of 0.3<NA<0.6, the low NA component and the high NA component are mixed in the light. Accordingly, by not detecting the light in this NA range, the mixing of the forward scattered component 7b into the scattered light detector 47 for detecting the high NA component can be reduced. As a result, the SN ratio in the scattered light detectors 47 and 49 can be improved.

In this case, the NA separating mask 45 may be configured as shown in FIG. 3, wherein a transmitting area 45a is provided at the central portion, an absorbing area 45b is provided around the transmitting area 45a, and a reflecting area 45c is provided around the absorbing area 45b. With this configuration, the transmitting area 45a transmits the forward scattered component 7b having a low numerical aperture and the reflecting area 45c reflects the side scattered component 7a having a high numerical aperture. As a result, only the forward scattered component 7b is detected by the detector 49 and only the side scattered component 7a is detected by the detector 47.

Alternatively, the transmitting area 45a and the reflecting area 45c may be interchanged. That is, a reflecting area may be provided at the central portion, an absorbing area may be provided around the reflecting area, and a transmitting area may be provided around the absorbing area. In this case, the reflecting area reflects a forward scattered component having a low numerical aperture and the transmitting area transmits a side scattered component having a high numerical aperture. As a result, the forward scattered component is detected by the detector 47 and the side scattered component is detected by the detector 49.

(Condenser Lenses 46 and 48)

The condenser lenses 46 and 48 function to condense the side scattered component 7a and the forward scattered component 7b toward the scattered light detectors 47 and 49, respectively. Examples of the condenser lenses 46 and 48 may include a convex lens, Fresnel lens, and spherical lens.

(Scattered Light Detectors 47 and 49)

The scattered light detector 47 functions to detect the side scattered component 7a generated from the sample, and the scattered light detector 49 functions to detect the forward scattered component 7b generated from the sample. Examples of the scattered light detectors 47 and 49 may include a PD, CCD, PMT, and power meter.

Operation of the Optical Measuring Device 1

There will now be described the operation of the optical measuring device 1, i.e., a method of measuring a sample such as minute particles by using the analytical chip 3 in the optical measuring device 1. The sample to be measured by the optical measuring device 1 may be selected from any objects generating the fluorescence 6 and the scattered light 7 by applying the exciting light 5. Examples of the sample may include minute particles such as cells or microbeads, virus, bacteria, and yeast. The sample may be modified by one or more fluorochromes.

In the optical measuring device 1 according to this preferred embodiment, the exciting light 5 is emitted from the light source 20 in the light applying section 2 toward the detection area 31 of the analytical chip 3 and thereby applied to the sample flowing in the microchannel of the analytical chip 3. At this time, the sample as an object to be measured flows in the microchannel so as to be arranged in a line, so that the exciting light 5 can be applied to the pieces of the sample individually. By applying the exciting light 5 to the sample, the scattered light 7 having the same wavelength as that of the exciting light 5 is generated from the sample, and the fluorescence 6 having a wavelength longer than that of the exciting light 5 is generated from the sample.

The scattered light 7 and the fluorescence 6 generated from the sample have very small signal intensities. Therefore, in order to accurately detect the scattered light 7 and the fluorescence 6, the exciting light 5 has to be separated off from the scattered light 7 and the fluorescence 6. In this respect, the exciting light 5 is removed from the incident light on the detecting section 4 by the exciting light shielding mask 41 after the incident light is trapped by the objective lens 40. More specifically, the exciting light 5 having a numerical aperture less than 0.1 is shielded by the reflecting area 41a provided at the central portion of the mask 41, and the scattered light 7 and the fluorescence 6 having a numerical aperture greater than or equal to 0.1 are passed through the mask 41 in the transmitting area 41b.

The fluorescence 6 is next passed through the LPF 42 and detected by the fluorescence detector (not shown). On the other hand, the scattered light 7 is reflected by the LPF 42 and passed through the relay lens system (the lenses 43a and 43b) configured so as to form a conjugate plane with respect to the pupil of the objective lens 40. The scattered light 7 is next separated into the side scattered component 7a and the forward scattered component 7b by the NA separating mask 45. With this arrangement, NA separation can be performed at an optical position where the influence of focal shift and lateral offset occurring on the focal plane of the objective lens 40 is reduced. Accordingly, the side scattered component 7a and the forward scattered component 7b can be separated from each other with high accuracy.

More specifically, the low NA component is transmitted (or reflected) and the high NA component is reflected (or transmitted) by the NA separating mask 45. The low NA component is next supplied through the condenser lens 48 to the scattered light detector 49, and the high NA component is next supplied through the condenser lens 46 to the scattered light detector 47. In the scattered light detector 47, the intensity of the side scattered component 7a is measured to obtain information on the form and internal structure of the sample (cell), for example. On the other hand, in the scattered light detector 49, the intensity of the forward scattered component 7b is measured to obtain information on the size of the sample, for example.

The scattered light 7 has a property such that the forward directivity is increased with an increase in size of the sample (minute particle) and that side scattering and backward scattering are reduced. The light scattering phenomenon by a particle having a size greater than or equal to the wavelength of light is referred to as Mie scattering. In particular, when the particle size (diameter) is relatively large as ten times or more the wavelength of the exciting light 5 and the scattering angle is relatively small, Mie scattering can be approximated by Fraunhofer diffraction.

It is generally known that the forward scattered component 7b includes much scattering information (Fraunhofer diffraction) depending upon the outer diameter of a particle and that the side scattered component 7a includes much internal information (Mie scattering) on the fine structure of a particle. The high NA component on the downstream side of the mask 45 (with respect to the traveling direction of the exciting light 5) has a scattering angle larger than that of the low NA component. Accordingly, the side scattered component 7a can be more detected from the high NA component.

If the numerical aperture as a reference for the high NA component is low in separating the high NA component from the low NA component, a large proportion of forward scattered component is contained in the high NA component. In this case, a side scattered component can be obtained by subtracting the product of the low NA component and an arbitrary coefficient k (k is a positive number) from the high NA component as in the following expression.

(side scattered component)=(high NA component)−
k×(low NA component)         (1)

In the optical measuring device 1 according to this preferred embodiment, both the side scattered component 7a and the forward scattered component 7b generated from the sample are detected on the downstream side of the analytical chip 3 in the traveling direction of the exciting light 5. Accordingly, it is not necessary to detect scattered light on the front side of the analytical chip 3 (on the upstream side of the analytical chip 3 in the traveling direction of the exciting light 5). As a result, an optical system for backward scattering detection (detection of side scattered light on the upstream side of the analytical chip 3 in the traveling direction of the exciting light 5) can be eliminated and axial adjustment in the optical system can also be eliminated.

Further, in the optical measuring device 1 according to this preferred embodiment, two focal points have to be adjusted. That is, the focal point for the exciting light 5 and the focal point for the forward scattered component 7b and the fluorescence 6 have to be adjusted, so that the axial adjustment can be easily made. Further, the number of optical axes to be adjusted is smaller than that in the existing art, stabilization of the device 1 and a cost reduction can be realized.

In the existing art, side scattered light is detected by a PMT on the upstream side of an analytical chip in the traveling direction of the exciting light because the signal intensity is low. To the contrary, in the optical measuring device 1 according to this preferred embodiment, side scattered light can be detected by a PD on the downstream side of the analytical chip 3 in the traveling direction of the exciting light 5 because the signal intensity is high. Accordingly, the configuration of the detecting section 4 can be made compact, so that the device 1 can be reduced in size and cost.

Further, in the case of measuring minute particles such as cells by using the analytical chip 3 to detect side scattered light on the upstream side of the chip 3 in the traveling direction of the exciting light 5 at a given angle thereto, there is a possibility of coma aberration due to an error in thickness of the chip 3, causing a large influence on the detection accuracy. To the contrary, in the case of detecting side scattered light on the downstream side of the chip 3 in the traveling direction of the exciting light 5 as in this preferred embodiment, the influence of the thickness of the chip 3 can be reduced. Accordingly, although the analytical chip 3 is used, the measurement can be made with high accuracy.

2. Second Preferred Embodiment

General Configuration of the Optical Measuring Device 11

Figure 4:
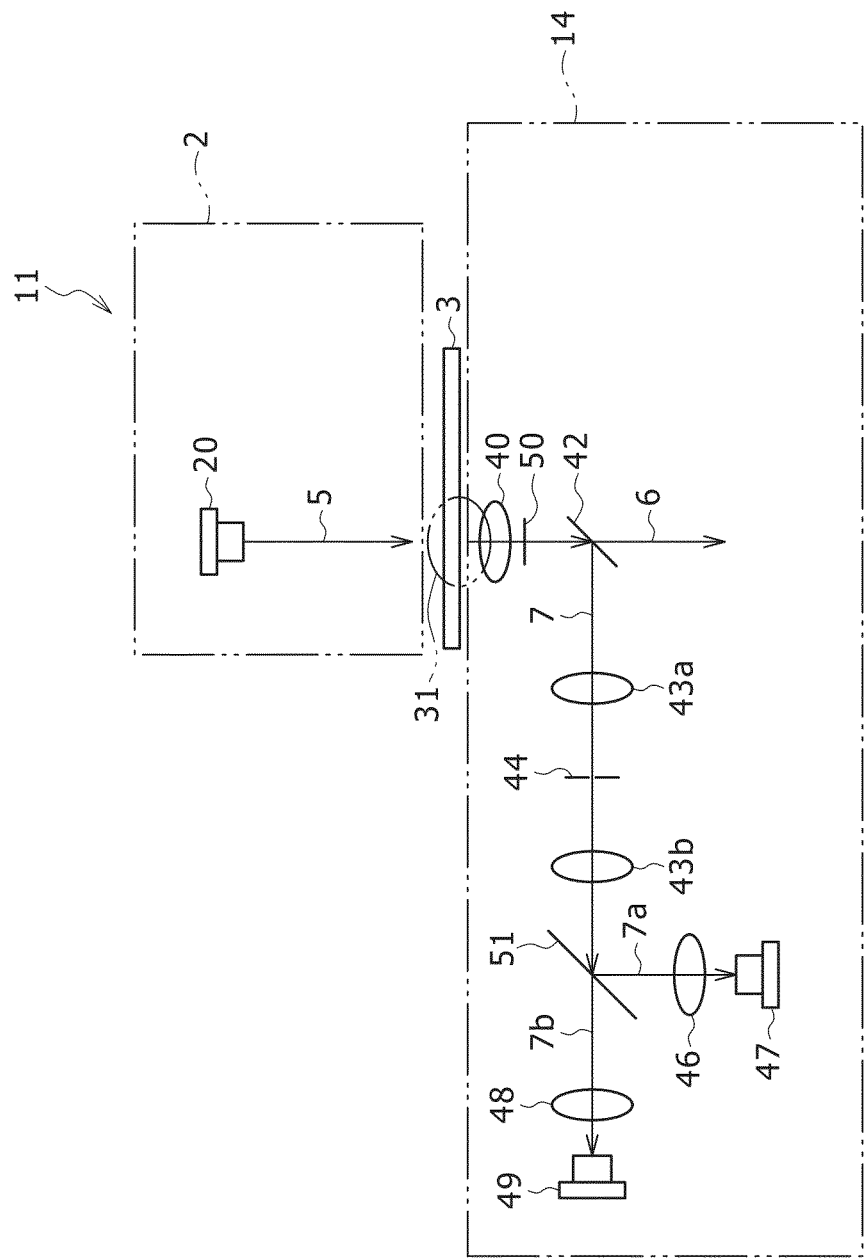
FIG. 4 is a schematic diagram showing the configuration of an optical measuring device according to a second preferred embodiment.

FIG. 4 is a schematic diagram showing the configuration of an optical measuring device 11 according to a second preferred embodiment. In FIG. 4, the same parts as those of the optical measuring device 1 according to the first preferred embodiment are denoted by the same reference numerals, and the detailed description thereof will be omitted herein. As shown in FIG. 4, the optical measuring device 11 is similar to the optical measuring device 1 according to the first preferred embodiment except that an NA separating mask 50 is provided in place of the exciting light shielding mask 41 in a detecting section 14 and that an NA separating mirror 51 is provided in place of the NA separating mask 45 in the detecting section 14.

NA Separating Mask 50

Figure 5:
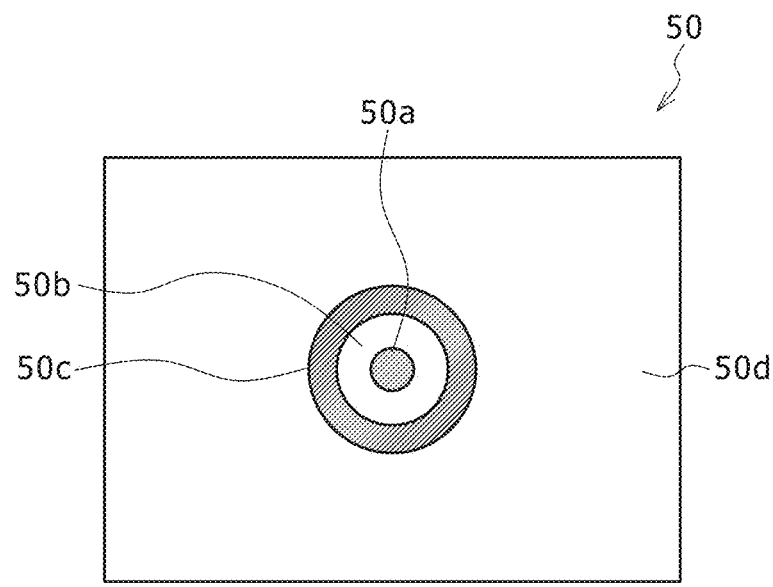
FIG. 5 is a schematic view showing the configuration of an NA separating mask used in the second preferred embodiment.

FIG. 5 is a schematic view showing the configuration of the NA separating mask 50. The NA separating mask 50 functions to remove the exciting light 5 and a mixed region of the side scattered component 7a and the forward scattered component 7b from the light trapped by the objective lens 40. More specifically, the NA separating mask 50 may be configured so that the component having a numerical aperture less than 0.1 and the component having a numerical aperture greater than 0.3 and less than 0.6 are reflected, and the component having a numerical aperture of 0.1 to 0.3 and the component having a numerical aperture greater than or equal to 0.6 are transmitted.

For example, as shown in FIG. 5, the NA separating mask 50 may be configured so that a reflecting area 50a is provided at the central portion, a transmitting area 50b is provided around the reflecting area 50a, a reflecting area 50c is provided around the transmitting area 50b, and a transmitting area 50d is provided around the reflecting area 50c. With this configuration, the fluorescence 6, the side scattered component 7a, and the forward scattered component 7b are transmitted, whereas the exciting light 5 and the mixed region of the side scattered component 7a and the forward scattered component 7b are reflected. As a result, only the fluorescence 6, the side scattered component 7a, and the forward scattered component 7b as the objects to be detected can be allowed to enter the LPF 42.

NA Separating Mirror 51

Figure 6:
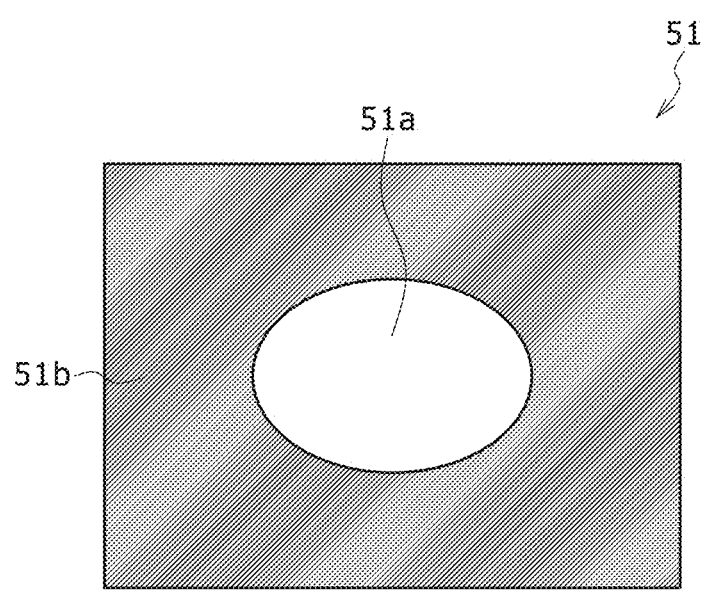
FIG. 6 is a schematic view showing the configuration of an NA separating mirror used in the second preferred embodiment.

FIG. 6 is a schematic view showing the configuration of the NA separating mirror 51. The NA separating mirror 51 functions to separate the incident scattered light 7 into the side scattered component 7a and the forward scattered component 7b. For example, the NA separating mirror 51 may be configured so as to transmit a low NA component having a numerical aperture less than 0.6 and reflect a high NA component having a numerical aperture greater than 0.6. In this case, the NA separating mirror 51 may be configured so that a transmitting area 51a is provided at the central portion and a reflecting area 51b is provided around the transmitting area 51a. With this configuration, only the forward scattered component 7b is detected by the detector 49, and only the side scattered component 7a is detected by the detector 47.

Operation of the Optical Measuring Device 11

The operation of the optical measuring device 11 according to this preferred embodiment will now be described. In the optical measuring device 11, the light incident on the detecting section 14 is trapped by the objective lens 40, and the exciting light 5 and the mixed region of the side scattered component 7a and the forward scattered component 7b are removed from the light incident on the detecting section 14 by the NA separating mask 50. More specifically, the exciting light 5 having a numerical aperture less than 0.1 is shielded by the reflecting area 50a provided at the central portion of the mask 50, and the scattered light 7 and the fluorescence 6 having a numerical aperture greater than or equal to 0.1 are passed through the mask 50 in the transmitting areas 50b and 50d, wherein the mixed region of the side scattered component 7a and the forward scattered component 7b is shielded by the reflecting area 50c.

The fluorescence 6 is next passed through the LPF 42 and detected by the fluorescence detector (not shown). On the other hand, the scattered light 7 (the side scattered component 7a and the forward scattered component 7b) is reflected by the LPF 42 and passed through the relay lens system (the lenses 43a and 43b) configured so as to form a conjugate plane with respect to the pupil of the objective lens 40. The scattered light 7 is next separated into the side scattered component 7a and the forward scattered component 7b by the NA separating mirror 51. With this arrangement, NA separation can be performed at an optical position where the influence of focal shift and lateral offset occurring on the focal plane of the objective lens 40 is reduced. Accordingly, the side scattered component 7a and the forward scattered component 7b can be separated from each other with high accuracy.

More specifically, the low NA component is transmitted (or reflected) and the high NA component is reflected (or transmitted) by the NA separating mirror 51. The low NA component is next supplied through the condenser lens 48 to the scattered light detector 49, and the high NA component is next supplied through the condenser lens 46 to the scattered light detector 47. In the scattered light detector 47, the intensity of the side scattered component 7a is measured to obtain information on the form and internal structure of the sample (cell), for example. On the other hand, in the scattered light detector 49, the intensity of the forward scattered component 7b is measured to obtain information on the size of the sample, for example.

In the optical measuring device 11 according to this preferred embodiment, not only the exciting light 5, but also the mixed region of the side scattered component 7a and the forward scattered component 7b is shielded by the NA separating mask 50 located on the upstream side of the LPF 42. Accordingly, the side scattered component 7a and the forward scattered component 7b can be separated from each other with high accuracy by the NA separating mirror 51.

The other configuration, operation, and effect of the optical measuring device 11 are similar to those of the optical measuring device 1 according to the first preferred embodiment.

3. Third Preferred Embodiment

General Configuration of the Optical Measuring Device 12

Figure 7:
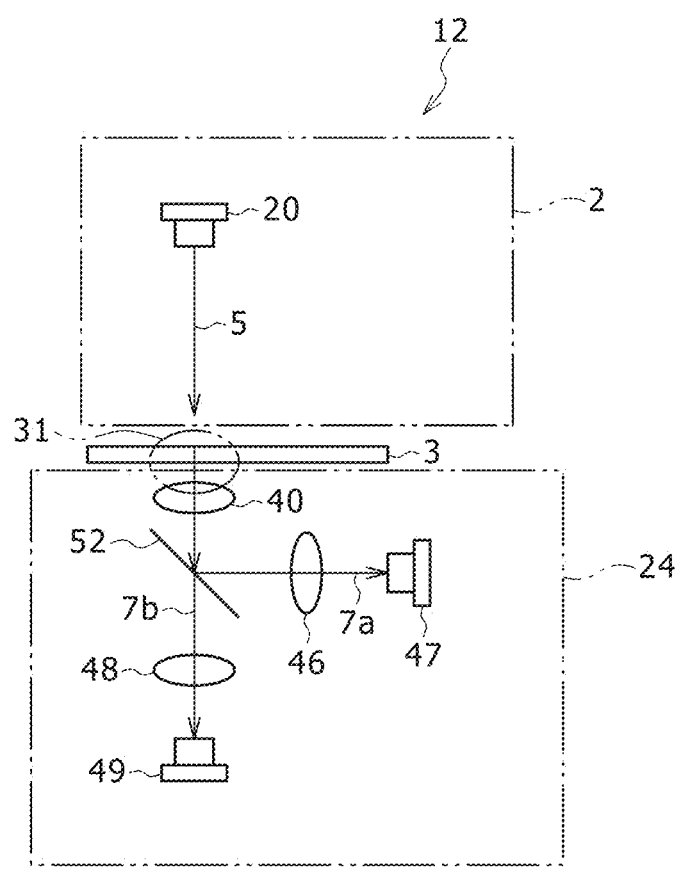
FIG. 7 is a schematic diagram showing the configuration of an optical measuring device according to a third preferred embodiment.

While both the fluorescence 6 and the scattered light 7 are detected in the first and second preferred embodiments mentioned above, the present application is not limited to these preferred embodiments, but applicable also to a device designed not to detect the fluorescence 6. FIG. 7 is a schematic diagram showing the configuration of an optical measuring device 12 according to a third preferred embodiment. In FIG. 7, the same parts as those of the optical measuring device 1 according to the first preferred embodiment are denoted by the same reference numerals, and the detailed description thereof will be omitted herein. As shown in FIG. 7, the optical measuring device 12 has a detecting section 24 configured so as to detect only scattered light.

Configuration of the Detecting Section 24

The detecting section 24 functions to detect the scattered light generated from the sample irradiated with the exciting light 5. The detecting section 24 essentially includes scattered light detectors 47 and 49 for detecting the scattered light generated from the sample. An objective lens 40, an NA separating mask 52, and condenser lenses 46 and 48 are provided between the sample and the scattered light detectors 47 and 49 so as to be arranged in this order from the sample side.

In the optical measuring device 12, the NA separating mask 52 is located at the pupil of the objective lens 40 to separate the incident scattered light into a side scattered component 7a and a forward scattered component 7b. Accordingly, no relay lens system is required.

NA Separating Mask 52

Figure 8:
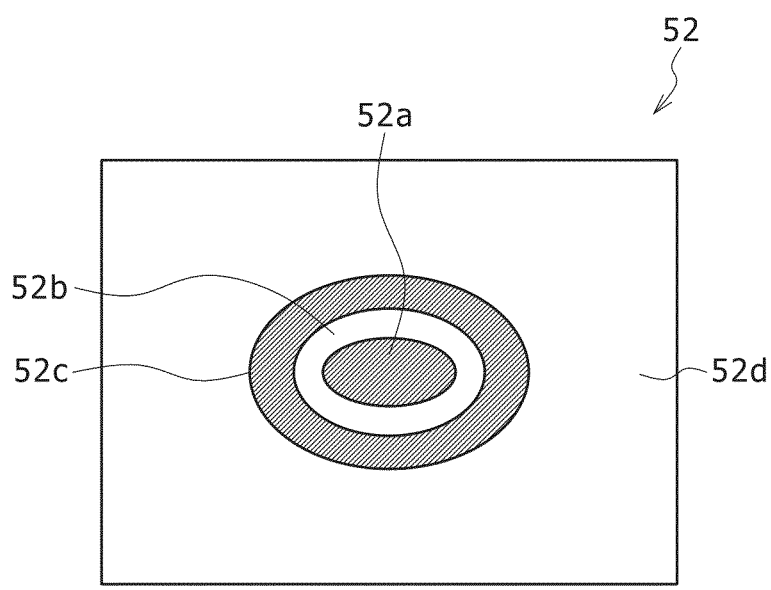
FIG. 8 is a schematic view showing the configuration of an NA separating mask used in the third preferred embodiment.

FIG. 8 is a schematic diagram showing the configuration of the NA separating mask 52. The NA separating mask 52 functions to remove the exciting light 5 and a mixed region of the side scattered component 7a and the forward scattered component 7b from the light trapped by the objective lens 40 and also to separate the side scattered component 7a and the forward scattered component 7b from each other. More specifically, the NA separating mask 52 may be configured so that the component having a numerical aperture less than 0.1 and the component having a numerical aperture greater than 0.3 and less than 0.6 are absorbed, the component having a numerical aperture of 0.1 to 0.3 is transmitted (or reflected), and the component having a numerical aperture greater than or equal to 0.6 is reflected (or transmitted).

For example, as shown in FIG. 8, the NA separating mask 52 may be configured so that an absorbing area 52a is provided at the central portion, a transmitting area 52b is provided around the absorbing area 52a, an absorbing area 52c is provided around the transmitting area 52b, and a reflecting area 52d is provided around the absorbing area 52c. With this configuration, the exciting light 5 and the mixed region of the side scattered component 7a and the forward scattered component 7b are absorbed, or removed by the NA separating mask 52. The side scattered component 7a having a high numerical aperture is reflected by the NA separating mask 52 to enter the detector 47. On the other hand, the forward scattered component 7b having a low numerical aperture is transmitted by the NA separating mask 52 to enter the detector 49.

Alternatively, the transmitting area 52b and the reflecting area 52d may be interchanged. That is, a reflecting area may be provided around the absorbing area 52a and a transmitting area may be provided around the absorbing area 52c. In this case, a forward scattered component having a low numerical aperture is reflected by the NA separating mask 52 to enter the detector 47, whereas a side scattered component having a high numerical aperture is transmitted by the NA separating mask 52 to enter the detector 49.

Operation of the Optical Measuring Device 12

The operation of the optical measuring device 12 according to this preferred embodiment will now be described. In the optical measuring device 12, the light incident on the detecting section 24 is trapped by the objective lens 40, and the exciting light 5 and the mixed region of the side scattered component 7a and the forward scattered component 7b are removed by the NA separating mask 52 located at the pupil of the objective lens 40. At the same time, the side scattered component 7a and the forward scattered component 7b are separated from each other by the NA separating mask 52. Thereafter, the side scattered component 7a and the forward scattered component 7b are detected by the detectors 47 and 49, respectively.

In the case of using the NA separating mask 52 shown in FIG. 8, the exciting light 5 having a numerical aperture less than 0.1 is shielded by the absorbing area 52a, and the mixed region of the side scattered component 7a and the forward scattered component 7b is shielded by the absorbing area 52c. Further, the low NA component (forward scattered component 7b) having a numerical aperture of 0.1 to 0.3 is transmitted by the transmitting area 52b, next condensed by the condenser lens 48, and then detected by the detector 49. On the other hand, the high NA component (side scattered component 7a) having a numerical aperture greater than or equal to 0.6 is reflected by the reflecting area 52d, next condensed by the condenser lens 46, and then detected by the detector 47.

In the optical measuring device 12 according to this preferred embodiment, the NA separating mask 52 is located at the pupil of the objective lens 40 to separate the side scattered component 7a and the forward scattered component 7b from each other. Accordingly, no relay lens system is required. The other configuration, operation, and effect of the optical measuring device 12 are similar to those of the first and second preferred embodiments.

Example

Figure 9:
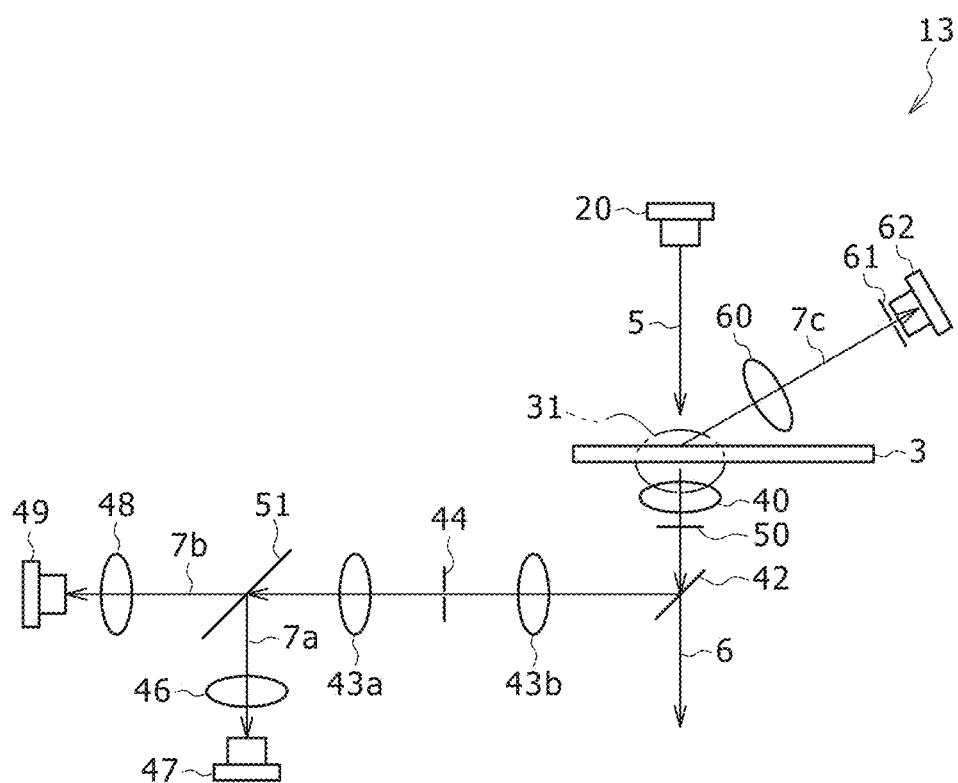
FIG. 9 is a schematic diagram showing the configuration of an optical measuring device used in Example.

The effect of the present application will now be described more specifically. FIG. 9 is a schematic diagram showing the configuration of an optical measuring device 13 used in Example. In Example, the optical measuring device 13 was used to measure side scattered light 7a on the downstream side of the analytical chip 3 in the traveling direction of the exciting light 5 and also to measure side scattered light 7c on the upstream side of the chip 3 in the traveling direction of the exciting light 5. The results of this measurement for the side scattered light 7a and the side scattered light 7c were compared.

The optical measuring device 13 includes an NA separating mask 50 and an NA separating mirror 51. The NA separating mask 50 is configured so that the component having a numerical aperture of 0.1 to 0.3 and the component having a numerical aperture greater than or equal to 0.6 are transmitted, whereas the component having a numerical aperture less than 0.1 and the component having a numerical aperture greater than 0.3 and less than 0.6 are reflected. The NA separating mirror 51 is configured so that the component having a numerical aperture less than 0.6 is transmitted and the component having a numerical aperture greater than or equal to 0.6 is reflected. Accordingly, the component having a numerical aperture greater than or equal to 0.6 is allowed to enter the scattered light detector 47, and the component having a numerical aperture of 0.1 to 0.3 is allowed to enter the scattered light detector 49.

The optical measuring device 13 further includes a scattered light detector 62 provided on the upstream side of the chip 3 in the traveling direction of the exciting light 5. A PMT was used as the scattered light detector 62, and a PD was used as each of the scattered light detectors 47 and 49 provided on the downstream side of the chip 3. Two f90 lenses (lenses 43a and 43b) were used as the relay lens system. The pinhole 44 has a diameter of 0.8 mm. Further, a condenser lens 60 and a pinhole 61 were provided between the chip 3 and the scattered light detector 62 for detecting the side scattered light 7c.

Figure 10A:
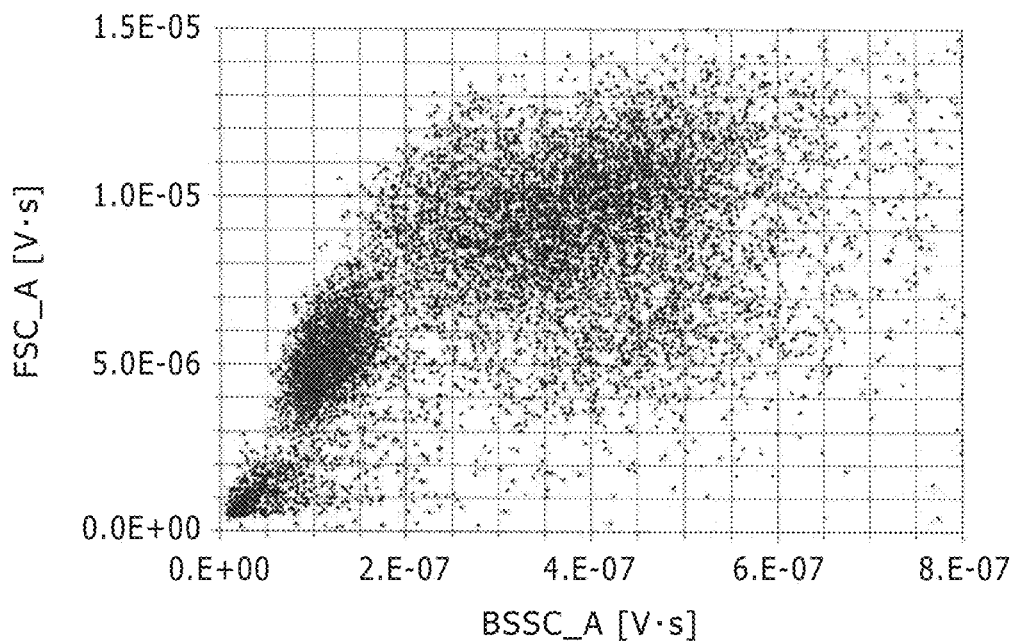
FIGS. 10A and 10B are graphs showing the results of detection of side scattered light by the use of the optical measuring device shown in FIG. 9.
Figure 10B:
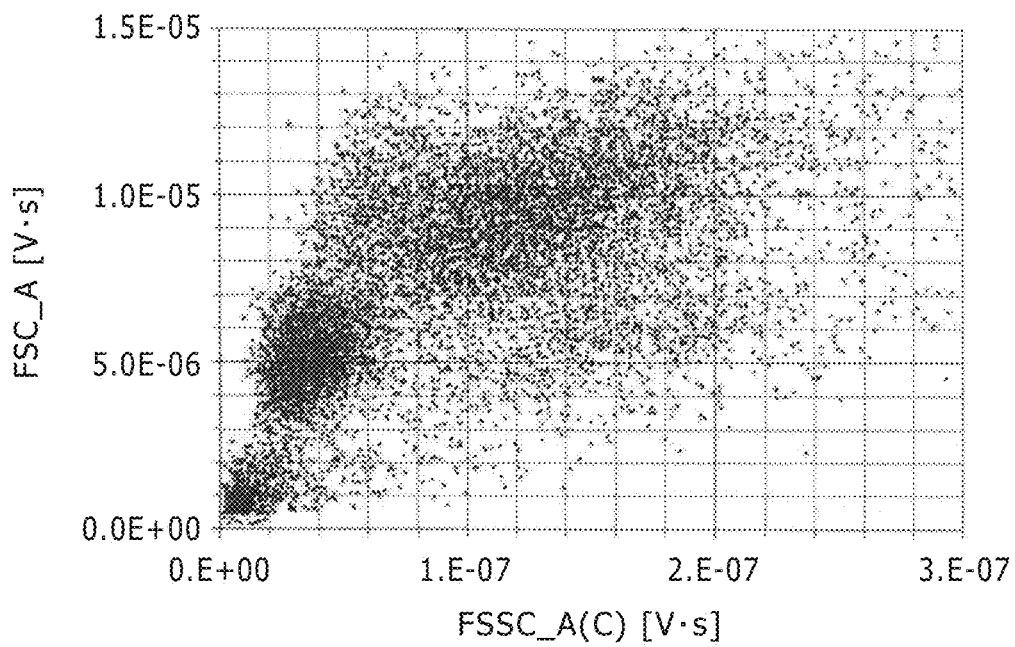
Figure 11:
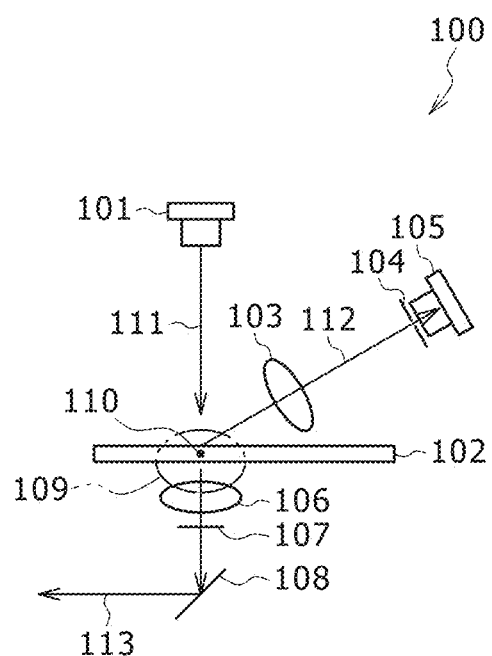
FIG. 11 is a schematic diagram showing the configuration of an existing optical measuring device having a mechanism for measuring side scattered light.

FIGS. 10A and 10B are graphs showing the results of detection of the side scattered lights 7a and 7c by the use of the optical measuring device 13 shown in FIG. 9. FIG. 10A shows the comparison between the forward scattered component 7b (the component having a numerical aperture of 0.1 to 0.3) and the side scattered component 7c measured on the upstream side of the chip 3 in the traveling direction of the exciting light 5. On the other hand, FIG. 10B shows the comparison between the forward scattered component 7b and the side scattered component 7a measured on the downstream side of the chip 3 in the traveling direction of the exciting light 5. As apparent from FIGS. 10A and 10B, the result of measurement of the side scattered component 7a is similar to the result of measurement of the side scattered component 7c.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. An optical measuring device comprising:
    a light applying section including a light source and configured to apply exciting light to a sample flowing in a channel; and
    a scattered light detecting section configured to detect scattered light generated from said sample irradiated with said exciting light on the downstream side of said sample in the traveling direction of said exciting light; and
    said scattered light detecting section including:
        a scattered light separating mask including a transmitting area, a reflecting area and an absorbing area, said transmitting and reflecting areas arranged to separate said scattered light into a low numerical aperture component having a numerical aperture not greater than a specific value and a high numerical aperture component having a numerical aperture greater than said specific value;
        a first detector configured and arranged to detect said low numerical aperture component; and
        a second detector configured and arranged to detect said high numerical aperture component,
    wherein the absorbing area is arranged between the reflecting area and the transmitting area on the scattered light separating mask.

2. The optical measuring device according to claim 1, wherein said scattered light detecting section further comprises a relay lens system for forming a conjugate plane on said scattered light separating mask.

3. The optical measuring device according to claim 1, wherein the numerical aperture of said low numerical aperture component is not greater than 0.3.

4. The optical measuring device according to claim 1, wherein said scattered light separating mask reflects said low numerical aperture component having a numerical aperture not greater than 0.3 in the reflecting area, transmits said high numerical aperture component having a numerical aperture not smaller than 0.6 through the transmitting area, and absorbs the other component having a numerical aperture greater than 0.3 and less than 0.6 in the absorbing area.

5. The optical measuring device according to claim 1, wherein the transmitting area is arranged around the reflecting area on the scattered light separating mask.

6. The optical measuring device according to claim 1, further comprising an analytical chip having a microchannel, wherein said light applying section applies said exciting light to said sample flowing in said microchannel.

7. The optical measuring device according to claim 1, wherein said scattered light detecting section further comprises an exciting light shielding mask for removing said exciting light.

8. The optical measuring device according to claim 1, further comprising:
a fluorescence detecting section including at least one selected from the group consisting of a photo-diode, a charge coupled device and a photo-multiplier tube, and is configured to detect fluorescence generated from said sample irradiated with said exciting light; and
a filter provided between said sample and said fluorescence detecting section/said scattered light detecting section for separating said fluorescence and said scattered light from each other.

9. The optical measuring device according to claim 1, wherein the absorbing area is configured to absorb a component having a numerical aperture greater than said low numerical aperture component, and to absorb a component having a numerical aperture lower than said high numerical aperture.

10. The optical measuring device according to claim 1, wherein the reflecting area is arranged around the absorbing area on the scattered light separating mask.

11. An optical measuring method comprising:
applying exciting light to a sample as an object to be measured;
separating scattered light generated from said sample irradiated with said exciting light with a scattered light separating mask into a low numerical aperture component having a numerical aperture not greater than a specific value and a high numerical aperture component having a numerical aperture greater than said specific value on the downstream side of said sample in the traveling direction of said exciting light by transmitting a portion of the scattered light through a transmitting area of the scattered light separating mask, by reflecting a portion of the scattered light onto a reflecting area of the scattered light separating mask, and by absorbing a portion of the scattered light onto an absorbing area of the scattered light separating mask; and
detecting said low numerical aperture component and said high numerical aperture component separately;
obtaining information on a size of said sample with a first detector that that is used to detect the low numerical aperture component; and
obtaining information on a form or an internal structure of said sample with a second detector that that is used to detect the high numerical aperture component,
wherein the absorbing area is arranged between the reflecting area and the transmitting area on the scattered light separating mask.

12. The optical measuring method according to claim 11, wherein the reflecting area is arranged around the absorbing area on the scattered light separating mask.

13. An optical measuring device comprising:
light applying means for applying exciting light to a sample flowing in a channel; and
scattered light detecting means for detecting scattered light generated from said sample irradiated with said exciting light on the downstream side of said sample in the traveling direction of said exciting light;
said scattered light detecting means including:
a scattered light separating mask including a transmitting area, a reflecting area, and an absorbing area, said transmitting and reflecting areas arranged to separate said scattered light into a low numerical aperture component having a numerical aperture not greater than a specific value and a high numerical aperture component having a numerical aperture greater than said specific value;
a first detector configured and arranged to detect said low numerical aperture component; and
a second detector configured and arranged to detect said high numerical aperture component,
wherein the absorbing area is arranged between the reflecting area and the transmitting area on the scattered light separating mask.

14. The optical measuring device according to claim 13, wherein the reflecting area is arranged around the absorbing area on the scattered light separating mask.

* * * * *